(12) United States Patent
Kane (10) Patent No.: US 11,298,379 B2
(45) Date of Patent: Apr. 12, 2022

(54) COMPOSITIONS COMPRISING MILK FAT GLOBULES AND METHODS OF MAKING SAME

(71) Applicant: James F. Kane, West Chester, PA (US)

(72) Inventor: James F. Kane, West Chester, PA (US)

(*) Notice: Subject to any disclaimer, the term of this patent is extended or adjusted under 35 U.S.C. 154(b) by 0 days.

(21) Appl. No.: 16/898,804

(22) Filed: Jun. 11, 2020

(65) Prior Publication Data

US 2021/0322481 A1 Oct. 21, 2021

Related U.S. Application Data

(60) Provisional application No. 63/011,045, filed on Apr. 16, 2020.

(51) Int. Cl.
| | |
|---|---|
| *A61K 35/20* | (2006.01) |
| *A61K 47/06* | (2006.01) |
| *A61K 9/00* | (2006.01) |
| *A61K 9/06* | (2006.01) |
| *A61K 9/14* | (2006.01) |

(52) U.S. Cl.
CPC ............ *A61K 35/20* (2013.01); *A61K 9/0014* (2013.01); *A61K 9/0053* (2013.01); *A61K 9/06* (2013.01); *A61K 9/14* (2013.01); *A61K 47/06* (2013.01)

(58) Field of Classification Search
CPC .. A61K 49/0054; C08L 5/02; G01N 2333/42; G01N 2400/22; G01N 33/542; G01N 33/66; C08B 37/0021
See application file for complete search history.

(56) References Cited

U.S. PATENT DOCUMENTS

| | | | |
|---|---|---|---|
| 5,703,051 A | 12/1997 | Berliner et al. | |
| 7,687,074 B2* | 3/2010 | Folan | A61P 31/12 424/535 |
| 10,028,987 B1 | 7/2018 | Pillsbury | |
| 2007/0154443 A1* | 7/2007 | Kalejman | A61K 8/986 424/74 |
| 2007/0270377 A1* | 11/2007 | Kawakami | A61Q 11/00 514/54 |
| 2012/0289591 A1* | 11/2012 | Folan | A61Q 11/00 514/474 |
| 2015/0216902 A1* | 8/2015 | Fardoussi | A61P 17/02 424/405 |
| 2017/0020945 A1 | 1/2017 | Reillo et al. | |
| 2017/0312322 A1* | 11/2017 | Rohwer | A61P 31/04 |
| 2018/0207213 A1* | 7/2018 | Mcelvany | A61Q 19/001 |
| 2019/0167740 A1 | 6/2019 | Kane et al. | |

FOREIGN PATENT DOCUMENTS

WO WO-03051378 A2 * 6/2003 ............. A61P 17/00

OTHER PUBLICATIONS

Wolflel et al., Nature, vol. 581, May 28, 2020 (Year: 2020).*
Guerin et al., Crit Rev Food Sci Nutr. 2019;59(4):639-651 (Epub Nov. 3, 2017) (Year: 2017).*
Hamming et al., J.Pathol 2004; 203:631-637. (Year: 2014).*
Peterson et al., Biol Neonate 1998;74143-162. (Year: 1998).*
Clark et al., J. Med. Microbiol. vol. 29 (2000), 719-723 (Year: 2000).*
Screen capture of www.kellymom.com, "What affects the amount of fat or calories in mom's milk," accessed May 20, 2021 (Year: 2021).*
Bezelgues et al., Short Communication: Milk fat globule membrane as a potential delivery system for liposoluble nutrients, J. Dairy Sci. 92:2524-2528, doi:10.3168/jds.2008-1725, American Dairy Science Association, 2009.
Lopez et al., Human milk fat globules: Polar lipid composition and in situ structural investigations revealing the heterogeneous distribution of proteins and the lateral segregation of sphingomyelin in the biological membrane, INRA, Agrocampus Ouest, UMR 1253 Science et Technologie du Lair et de l'Oeuf, F-35000 Rennes, France, Colloids and Surfaces B: Biointerfaces 83 (2011) 29-41.
Lipophilic Microconstiutents of Milk (see website article (Abstract), http://link.springer.com/chapter/10.1007/978-0-387-74087-4_3, pp. 1-21, copyright information 2008) (Year: 2008).

(Continued)

*Primary Examiner* — Robert S Cabral
(74) *Attorney, Agent, or Firm* — Kilyk & Bowersox, P.L.L.C.

(57) ABSTRACT

Compositions including anti-viral compositions, therapeutic compositions, sunscreen compositions, skin treatment compositions, anti-aging compositions, and methods of making the same, are provided. Each composition includes milk fat globules (MFG) and may contain one or more agents encapsulated by the MFG. The unique nature of MFG provides an intact mammalian membrane containing proteins, glycoproteins, and carbohydrates found in mammary cells. By treating an infected patient with MFG, the MFG serve as a surrogate cell and interact with enveloped viruses, such as the COVID-19 coronavirus, the Herpes virus, and the Epstein Barr Virus, rendering them non-infectious. MFG derived from mammals can also be used to deliver pharmaceutical materials into an animal body such that the pharmaceutical materials bypass the venous blood and enter directly into the animal's lymphatic system. MFG allow the delivery of materials orally that could not heretofore have been delivered efficiently.

20 Claims, 6 Drawing Sheets

(56) References Cited

OTHER PUBLICATIONS

Khan et al., "Advanced drug delivery to the lymphatic system: lipid-based nanoformulations," International Journal of Nanomedicine, 8, 2013: pp. 2733-2744.
Argov et al. "Milk Fat Globule structure & function; nanosciece comes to milk production," National Institutes of Health, Trends Food Sci Technol. 19(12), Dec. 2008., pp. 1-13.
Black, Dennis D., "Development and Physiological Regulation of Intestinal Lipid Absorption. I. Development of Intestinal lipid absorption: cellular events in chylomicron assembly and secretion," Am J Physiol Gastrointest Liver Physiol, vol. 293, May 10, 2007, pp. G519-G524.
Cano-Ruiz et al., "Effect of Homogenization Pressure on the Milk Fat Globule Membrane Proteins," Journal of Dairy Science, vol. 80, No. 11, 1997, pp. 2732-2739.
Dewettinck et al., "Nutritional and technological aspects of milk fat globule membrane material," International Dairy Journal, vol. 18, issue 5, revised Jul. 6, 2007, pp. 436-457.
Kailasapathy, Kasipathy, "Chemical Composition, Physical, and Functional Properties of Milk and Milk Ingredients," Dairy Processing and Quality Assurance, 2nd edition, 2016, pp. 77-105.
Lopez et al., "Lipid droplets coated with milk fat globule membrane fragments: Microstructure and functional properties as a function of pH," Food Research International, 91, 2017, pp. 26-37.
Michalski et al., "The supramolecular structure of milk fat influences plasma triacylglycerols and fatty acid profile in the rat," European Journal of Nutrition, vol. 45, No. 4; 2006, pp. 215-224.
Rosqvist et al., "Potential role of milk fat globule membrane in modulating plasma lipoproteins, gene expression, and cholesterol metabolism in humans: a randomized study," The American Journal of Clinical Nutrition, vol. 102, issue 1, Jul. 1, 2015, pp. 20-30.
Smoczyński et al., "Composition and Structure of the Bovine Milk Fat Globule Membrane—Some Nutritional and Technological Implications," Food Reviews International, 28, 2012: pp. 188-202.
Thompson Gilbert, "Absorption of fat-soluble vitamins and sterols," J clin Path., 24, Suppl. (Roy. Coll. Path.), 5: pp. 85-89.
Mohan Maneesha Sheenu, "Casein Micelles and their Properties: Polydispersity, Association with Vitamin A and Effect of Ultra-High Pressure Homogenization," University of Tennessee—Knoxville, Trace: Tennessee Research and Creative Exchange, Aug. 2014.
Wang et al., "In Search of Preventative Strategies: Novel Anti-Inflammatory High-CBD Cannabis Sativa Extracts Modulate ACE2 Expression in COVID-19 Gateway Tissues," doi:10.20944/preprints202004.0315.v1, posted Apr. 19, 2020.
Panzella et al., "Red human hair pheomelanin is a potent pro-oxidant mediating UV-independent contributory mechanisms of melanomagenesis," Journal of International Federation of Pigment Cell Societies: Pigment Cell & Melanoma Research; vol. 27, Issue 2, pp. 244-252, doi.10.1111/pcmr.12199.
Kanchi et al., "Tocotrienols: the unsaturated sidekick shifting new paradigms in vitamin E therapeutics," Drug Discovery Today; vol. 22, No. 12, Dec. 2017, pp. 1765-1781.
"Key Statistics for Melanoma Skin Cancer," American Cancer Society; last revised Jan. 8, 2020.
Gardner, Stephanie S., "Retinoids: Anti-Aging Benefits," WebMD; https://www.webmd.com/beauty/ss/slideshow-retinoids-for-aging; Medically Reviewed Oct. 19, 2019, 11 pages.
Hanson et al., "Sunscreen enhancement of UV-induced reactive oxygen species in the skin,"ScienceDirect: Free Radical Biology & Medicine, vol. 41, revised May 17, 2006, pp. 1205-1212.
Meredith et al., "The physical and chemical properties of eumelanin," Journal Compilation: Pigment Cell Res.; vol. 19, 2006, pp. 572-594.
Yeager et al., "What's New in A Review of New Concepts and Controversies," Department of Dermatology, Henry Ford Medical Center, Dermatol Clin, vol. 37, 2019, pp. 149-157.
"Oxybenzone," Wikipedia, last edited Feb. 4, 2020, 9 pages.
Burnett et al., "Current sunscreen controversies: a critical review," Dermatology Service: Photodermatology, Photoimmunology & Photomedicine, vol. 27, 2011, pp. 58-67.
Hanson, Kerry., "Column: How the chemistry of sunscreen is protecting your skin this Memorial Day," The Conversation, May 25, 2017.
Doheny, Kathleen., "FDA Proposed Major Changes to Suncreen Rules," WebMD Heath News, reviewed on Feb. 21, 2019.
Hibler, et al., "Photoprotection and Skin Cancer Prevention," Dermatology Division, Springer International Publishing, Switzerland, 2016, pp. 23-38.
Wondrak et al., "Identification of Quenchers of Photoexcited States as Novel Agents for Skin Photoprotection," Department of Pharmacology and Toxicology, College of Pharmacy, Arizona Cancer Center, University of Arizona, vol. 312, No. 2, received Jul. 27, 2004, pp. 482-491.
Meyer et al., "Chapter 26: Agumenting Skin Photoprotection Beyond Sunscreens," Springer International Publishing, Switzerland, 2016, pp. 439-460.
"Avobenzone," Wikipedia, last edited Mar. 31, 2020, 7 pages.
"Homosalate," Wikipedia, last edited Oct. 6, 2019, 3 pages.
"Octyl salicylate," Wikipedia, last edited Jul. 28, 2019, 3 pages.
"Octocrylene," Wikipedia, last edited Oct. 22, 2019, 3 pages.
Ojala et al. "Herpes Simplex Virus Type 1 Entry into Host Cells: Reconstitution of Capsid Binding and Uncoating at the Nuclear Pore Complex In Vitro," Molecular and Cellular Biology, vol. 20, No. 13; Jul. 2000, pp. 4922-4931.
Akhtar et al. "Viral entry mechanisms: cellular and viral mediators of herpes simplex virus entry," National Institutes of Health, FEBS J. 276(24), Dec. 2009, pp. 7228-7236.
Rapraeger et al., "Cell Surface Proteoglycan Associates with the Cytoskeleton at the Basolateral Cell Surface of Mouse Mammary Epithelial Cells," The Journal of Cell Biology, vol. 103 (No. 6, Pt. 2), Dec. 1986, pp. 2683-2696.
"Chapter 13: The Digestive System (Chemical Digestion and Absorption: A Closer Look)," lumen: Anatomy and Physiology, pp. 1-16.

\* cited by examiner

COMPOSITIONS COMPRISING MILK FAT GLOBULES AND METHODS OF MAKING SAME

CROSS-REFERENCE TO RELATED APPLICATION

The present application claims priority to U.S. Provisional Patent Application No. 63/011,045, filed Apr. 16, 2020, which is incorporated herein in its entirety by reference.

BACKGROUND OF THE INVENTION

There is a need for a composition that can be used to inactivate enveloped viruses, such as Coronaviruses, for example, COVID-19 and Herpes viruses, for example, Herpes Simplex Virus and Epstein Barr Virus. There is also a need for a composition that can deliver a sunscreen formulation in a safe and effective manner.

Figure 1:
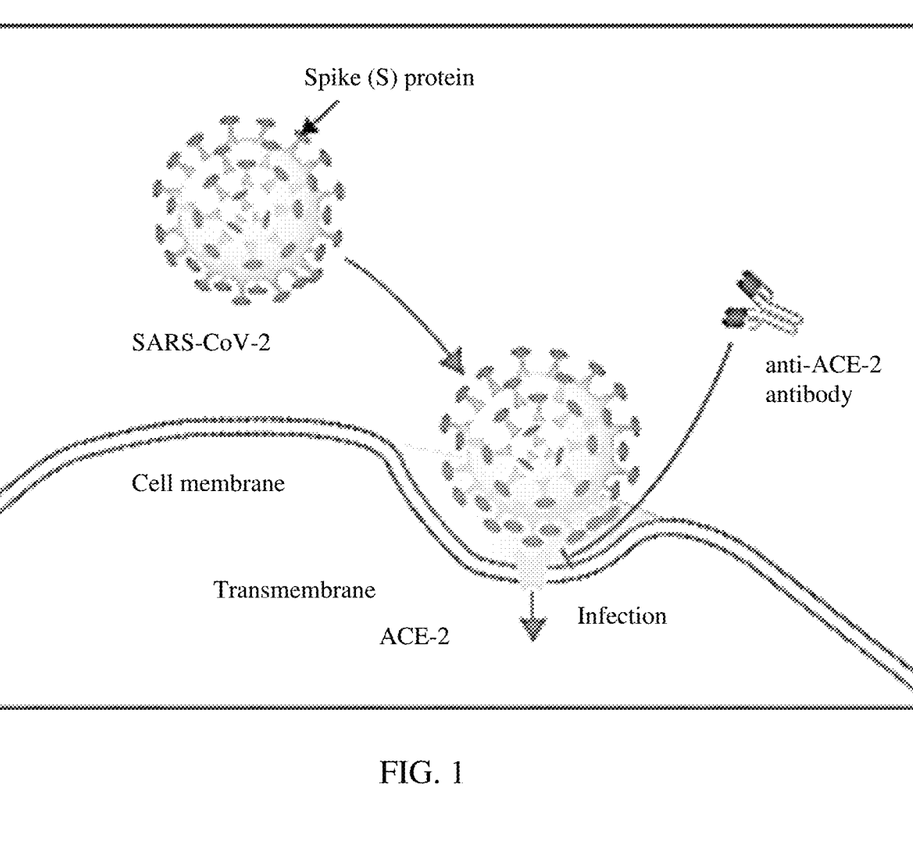

Many viruses contain an envelope, which is derived from a cell that the virus infects when it buds from that cell as a mature virion. These mature virions recognize some components on a cell membrane, which allows the mature virions to attach to the cell, after which the genetic material of the mature virion is injected into the cell. FIG. 1 shows an example of this event.

FIG. 1 is a schematic illustration showing how a coronavirus, specifically, the SARS-CoV-2 coronavirus, attaches to a cell membrane. First, like with the COVID-19 coronavirus, the SARS-CoV-2 coronavirus recognizes Angiotensin-converting enzyme 2 (ACE-2) in the cell membrane and binds to the cell membrane. ACE-2 lowers blood pressure by catalyzing the hydrolysis of angiotensin II (a vasoconstrictor peptide) into angiotensin (1-7) (a vasodilator). ACE-2 counters the activity of the related angiotensin-converting enzyme (ACE) by reducing the amount of angiotensin-II and increasing Ang (1-7). While subsequent events have not been clearly delineated, this initial binding is essential for infecting the cell.

Figure 2:
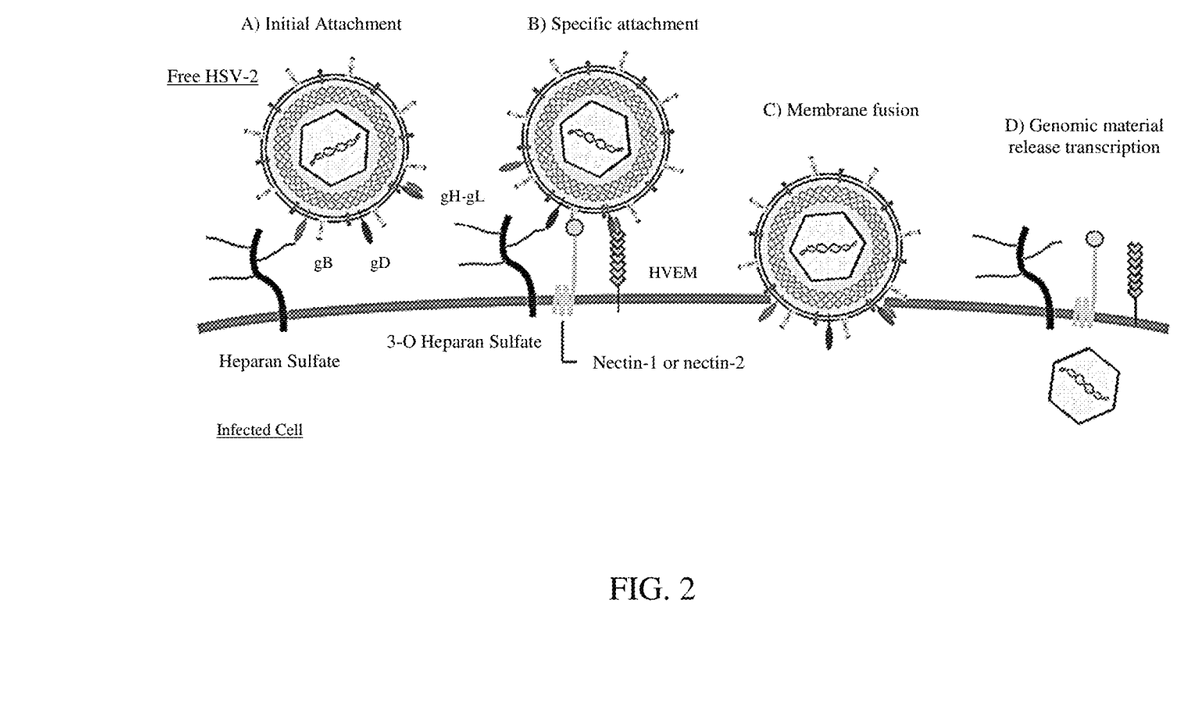
Figure 3:
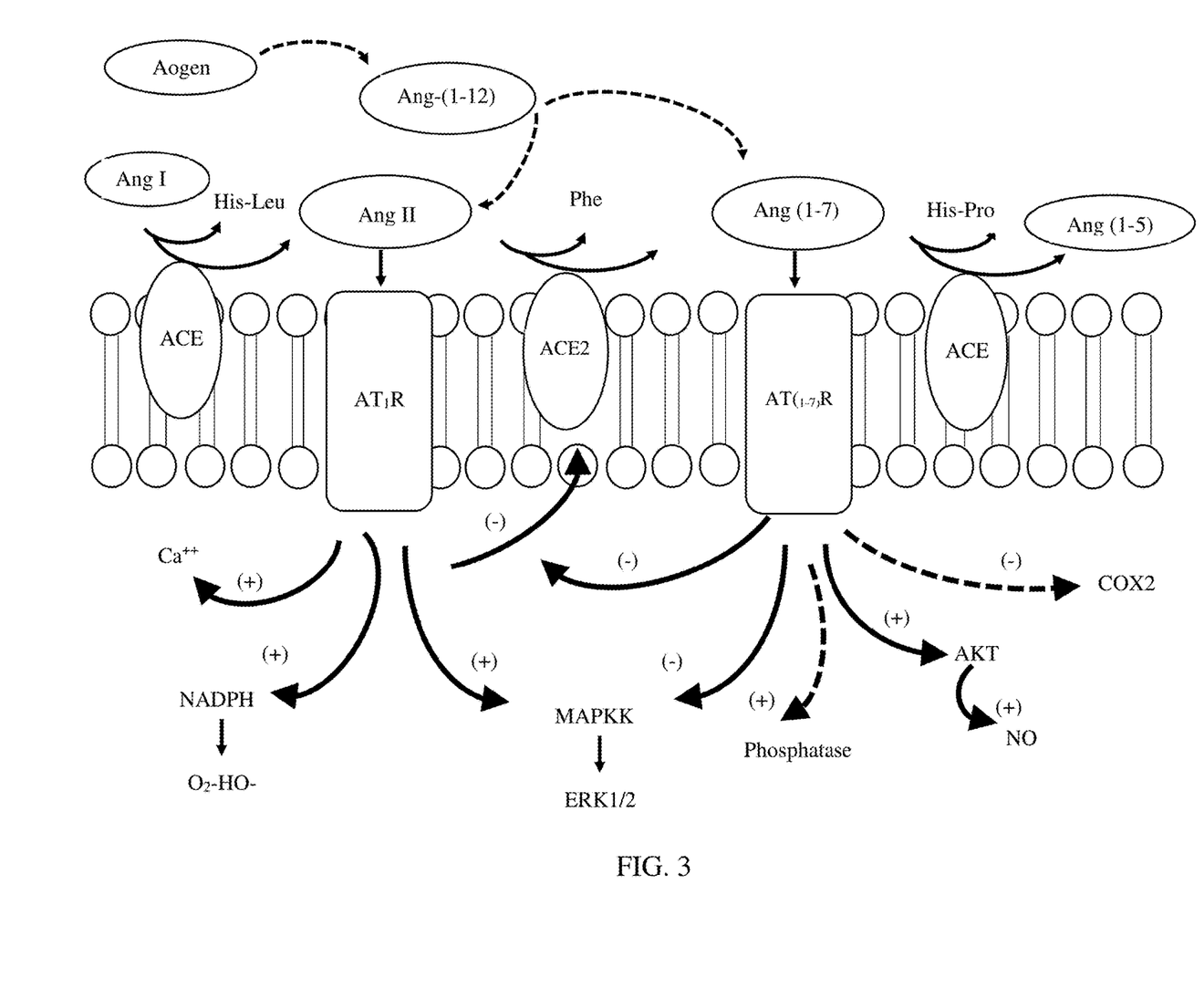

The Herpes viruses also use such a mechanism, but the initial interaction involves heparin sulfate as illustrated in FIG. 2. Herpes viruses are typically found on the surface of the skin, such as with genital herpes, oral herpes, and shingles.

Sunscreen formulations are designed to protect skin from light energy. Light energy arrives to earth in the form of photons some of which can be seen, for example, the visible colors, and some which cannot, for example, UV radiation and X-rays. Although the visible rays can do some damage to the skin, the major concerns from the perspective of sunburn are the UV rays. The UV rays are further subdivided into UVC from 200 nm-290 nm, UVB from 290 nm-320 nm, UVA2 from 320-340 and UVA1 from 340 nm-400 nm. About 95% of the UV rays reaching earth are UVA and 5% are UVB. The UV rays can penetrate the upper epidermal layer and enter the dermis where the energy of the photons needs to be dissipated. The effects of these energetic rays of light on the skin lead to several biological consequences. First, the UV energy can be used to form covalent bonds in the form of pyrimidine dimers in the DNA. Since these DNA aberrations would cause mutations during replication, the cells have repair mechanisms to eliminate these dimers before they can cause any damage. Second, these rays can be absorbed by the endogenous chromophores inside the cells with the subsequent production of photoexcited states and the generation of reactive oxygen species (ROS). This of itself is not an issue since there are systems in place to handle ROS because these molecules are normal by-products of cellular metabolism.

Problems arise, however, when the extent of UV rays reaches a point that exceeds the capacity of the cells in the body to respond to the stress of this radiation. For example, spending long times in the sun without adequate protection for your skin would lead to overburdening the cells capacity to respond to the insult.

In the United States, the Food and Drug Administration regulates sunscreens as drugs. Because the United States was historically most concerned with protecting against sunburn, 14 molecules that block sunburn-inducing UVB rays are approved for use. There are just two UVA-blocking molecules presently available in the United States: avobenzone, a chemical filter; and zinc oxide, a physical blocker. That there are just these two is a testament to the more recent understanding that UVA causes trouble, not just tans. There is a need for better sunscreen formulations.

Even the highest sun protection factor (SPF) sunscreens don't block 100 percent of UV rays. The addition of antioxidants has been used to supply a second line of protection when the skin's natural antioxidant defenses are overloaded. Some antioxidant ingredients include tocopheral acetate (Vitamin E), sodium ascorbyl phosphate (Vitamin C), and the photostabilizer DESM (also known as di-2,2'-diethylhexyl-3,5-dimethoxy-4-hydroxy-benzylidenemalonate, or diethylhexyl syringylidene malonate (INCI). Sunscreen researchers are beginning to investigate if the absorption of other colors of light, like infrared, by skin molecules, has a role to play in photodamage.

As research continues, one thing known for certain is that protecting DNA from UV damage, for people of every color, is synonymous with preventing skin cancers The Skin Cancer Foundation, the American Cancer Society, and the American Academy of Dermatology all stress that research shows regular use of an SPF 15 or higher sunscreen prevents sunburn and reduces the risk of non-melanoma cancers by 40 percent and melanoma cancers by 50 percent.

As stated in the WEBMD archives, the FDA has issued a long-awaited plan to update regulations for sunscreen products marketed in the US. An overview of these proposed rules is provided below. The Division of Nonprescription Drug Products in the FDA Center for Drug Evaluation and Research, has stated that the new rules include rules related to: active ingredients first; dosage forms; SPF; labelling; testing; and combination products.

Active Ingredient Safety

First, of the 16 currently marketed active ingredients, only two—zinc oxide and titanium dioxide—are safe and readily useful in sunscreens. Two other ingredients—PABA and trolamine salicylate—are not considered safe. PABA and trolamine salicylate ingredients are not currently in the U.S. market. There may be many ingredients for which there are insufficient data to make a positive, "generally regarded as safe and effective" (GRASE), determination.

Dosage Forms

Sprays, oils, lotions, creams, gels, butters, pastes, ointments, and sticks are considered GRASE. More information is needed on the safety of powders. Wipes, towelettes, body washes, shampoos, and other forms will be categorized as new drugs, as the FDA has not received data showing their eligibility yet.

SPF

The new rules would raise the maximum SPF (sun protection factor) value on labels from 50 plus, to 60 plus. The FDA may propose to permit products with SPF up to 80, 
to give manufacturers flexibility. Products with an SPF of 15 or higher must also provide broad-spectrum protection. As SPF increases, the protection against UVA rays must also increase.

Labeling

Active ingredients must be on the front of the product, to bring sunscreens in line with other over-the-counter (OTC) drugs. There should also be a notification on the front label to read the skin cancer and skin aging alert for products that have not been shown to help prevent skin cancers. The format for labeling SPF, broad spectrum, and water resistance will be revised.

Testing

The FDA will clarify expectations from the industry for testing and recordkeeping on products.

Combination Products

Products that combine sunscreen with insect repellents are not GRASE.

Topical formulations containing three unique classes of ingredients have emerged in the scientific literature to reduce the burden of sun-induced formation of ROS within skin, including: Sunscreens; Quenchers of photoexcited states (QPES); and Antioxidants (AOX). Nonetheless, there is a need for a better sunscreen formulation.

SUMMARY OF THE INVENTION

Compositions, for example, anti-viral compositions, therapeutic compositions, sunscreen compositions, skin treatment compositions, anti-aging compositions, and methods of making the same are provided by the present invention. The unique nature of the milk fat globules (MFG) provides for an intact and organized mammalian membrane containing proteins, glycoproteins, and carbohydrates found in mammary cell membranes. MFG obtain their membranes from mammary cells, and thus contain components associated with the initial interaction between a viral coat and a cell membrane. Thus, the interaction between a virus and MFG can lead to injection of the genetic material into the MFG, with or without the use or inclusion of other anti-viral agents, rendering the virus particle non-infectious. Thus, according to various embodiments of the present invention, MFG are used to serve as surrogate cells to interact with enveloped viruses, such as the COVID-19 coronavirus, and Herpes viruses, rendering such viruses non-infectious.

FIG. 3 is a schematic illustration of the membrane of a milk fat globule and shows the interaction of ACE-2 with Angiotensin. First, Angiotensinogen (Aogen) is converted into active angiotensins (1-12). The presence of ACE-2 enables an interaction between the MFG and the coronavirus causing inactivation of the virus.

For therapeutic, sunscreen, skin, and anti-aging compositions according to the present invention, each composition includes MFG and one or more agents encapsulated by the MFG. According to the present invention, MFG derived from mammals are used to deliver pharmaceutical materials orally into an animal body in such a manner that the pharmaceutical materials bypass the venous blood and enter directly into the animal's lymphatic system. This structure allows the molecules to deliver materials orally that could not heretofore be delivered efficiently. While there are plenty of synthetic liposomes and micelles, these do not contain the organizational structure of an MFG.

BRIEF DESCRIPTION OF THE DRAWINGS

The invention may be more fully understood with reference to the accompanying drawings. The drawings are intended to illustrate, not limit, the present teachings.

FIG. 1 is a schematic illustration showing the attachment of the SARS-CoV-2 coronavirus to a cell membrane.

FIG. 2 is a schematic illustration showing a sequence of the initial interaction of a Herpes virus with Heparin sulfate, the specific attachment of the virus, membrane fusion, and genomic material release transcription.

FIG. 3 is a schematic illustration of a membrane of a milk fat globule and shows the interaction of ACE-2 with Angiotensin.

FIG. 4 is a flow diagram and schematic illustration of the generation of random cellular damage and the initiation of specific signaling pathways that create metabolic dysfunction and skin photodamage.

FIG. 5 is a schematic illustration showing how sunscreens, quenchers of photoexcited states (QPES), and antioxidants (AOX), suppress formation of or scavenge of reactive oxygen species in human skin.

FIG. 6 shows the structures of various retinoids that can be formulated with MFG to create a pathway that enables an improved absorption of vitamin A into the skin.

DETAILED DESCRIPTION OF THE INVENTION

Methods according to the present invention can be used to make the compositions of the present invention, including, for example, milk fat globules (MFG) encapsulating anti-viral agents, therapeutic compounds, therapeutic compositions, or other compounds and compositions. The methods can include known encapsulating methods. The present invention takes advantage of the uniqueness of MFG to function as a carrier of compounds and materials for a variety of pharmaceutical and other applications. The MFG can be derived from mammals. Formulating lipophilic compounds with the MFG creates a unique delivery system and allows for lipophilic compounds to be delivered by a mechanism that evolved with the development of mammals. These structures are nature's way to deliver fat-soluble materials effectively to the blood stream.

The present invention also provides a method of forming a soluble form of a compound or composition. The method can comprise mixing together an anti-viral, therapeutic, or other, compound or composition, herein referred to as component (a), with a source of MFG, herein referred to as component (b). Components (a) and (b) can be mixed together to effect migration of component (a) into component (b). Component (a) can comprise a therapeutic agent, an anti-viral agent, a sunscreen agent, a skin treatment agent, an anti-aging agent, or a combination thereof. Component (b) can comprise fat globules from a mammalian source, animal source, plant source, synthetic source, or a combination thereof. The mixing can comprise stirring together at a rate of from about 5 rpm to about 12,000 rpm, for example, from about 5 rpm to about 5000 rpm, from about 10 rpm to about 1000 rpm, from about 50 rpm to about 800 rpm, or from about 100 rpm to about 500 rpm. The stirring can comprise mixing components (a) and (b) together to form a mixture and subjecting the mixture to centrifugation to effect migration of component (a) into component (b). The mixing can comprise mixing components (a) and (b) together to form a mixture and subjecting the mixture to sonication, homogenization, centrifugation, or the like, to effect migration of component (a) into component (b).

According to various embodiments of the present invention, component (b) can comprise a powder and component (a) can be mixed directly with the powder.

Component (a) and component (b) can be mixed together at a respective weight ratio of from 1:0.1 to 1:100, for example, from 1:0.5 to 1:50, from 1:1 to 1:20, from 1:1 to 1:10, from 1:2 to 1:8, or from 1:2 to 1:5, for a component (b) that comprises 100% by weight fat globules. Diluents, for example, water, deionized water, fruit juice, or the like, can also be added in amounts of from about 1% by weight or more, 3% by weight or more, or 5% by weight or more, based on the total weight of components (a) and (b) combined. Diluents can be added in amounts of from about 10% by weight or more, 20% by weight or more, 30% by weight or more, 40% by weight or more, 50% by weight or more, from 10% by weight to 95% by weight, from 20% by weight to 90% by weight, from 30% by weight to 85% by weight, or from 40% by weight to 80% by weight, based on the total weight of components (a) and (b) combined.

Component (a) and component (b) can be mixed together at a respective weight ratio of from 1:0.1 to 1:100, for example, from 1:0.5 to 1:50, from 1:1 to 1:20, from 1:1 to 1:10, from 1:2 to 1:8, or from 1:2 to 1:5, for a source of component (b) that contains from 1% by weight to 100% by weight milk fat, for example, from 2% by weight to 75% by weight milk fat, from 4% by weight to 66% by weight milk fat, from 10% by weight to 40% by weight milk fat or from 12% by weight to 38% by weight milk fat.

Various methods of making and processing milk fat globules and water-soluble compounds and compositions comprising the same, and various water-soluble compounds and compositions comprising milk fat globules, all of which can be used in embodiments of the present invention, are taught in U.S. Patent Application Publication No. US 2019/0167740 A1 to Kane et al., which is incorporated herein in its entirety by reference.

In various embodiments of the present invention, milk and milk products can be used as a source of fat globules. Milk is an emulsion comprising fat particles (globules) dispersed in an aqueous (watery) environment. The fat globules do not coalesce and form a separate layer (oil off or churn) because they are protected by a membrane layer that keeps the fat particles separated from the water phase. The principal group of milk proteins, the caseins, are not soluble in water and exist in milk as smaller particles (<300 nm) called micelles.

Herein, milk is defined as a dispersion of MFG (fat particles) and casein micelles (protein particles) dispersed in a continuous phase of water, sugar (lactose), whey proteins, and minerals.

Milk Plasma is defined herein as what is left after fat globules are separated out of milk; which is equivalent to skim milk for practical purposes.

Milk Serum is defined herein as what is left after both fat globules and casein micelles are taken away from milk; which is equivalent to cheese whey for most practical purposes.

Milk permeate is defined herein as what is left after fat globules, casein micelles, and whey proteins are taken away from milk.

The fat emulsion layer containing the MFG can be used according to embodiments of the present invention. Different structures are formed by the diverse nature of the MFG. Molecules of interest can be added to these diverse structures. The MFG can be used as such or can first be made more uniform by homogenization. Molecules of interest can be added, with or without homogenization of the MFG. Molecules of interest can be added, with homogenization of the MFG, before, during, or after homogenization.

These uniqueness of MFG enables them to deposit their fatty contents into an enterocyte in the small intestine. Once inside the fat coalesces and is extruded as a chylomicron migrating from the enterocyte into the lymph. It bypasses the portal vein and hence avoids the liver by being deposited into the arterial system.

Antiviral for Enveloped Viruses

According to various embodiments of the present invention, MFG are used as an anti-viral agent for enveloped viruses. Many viruses contain an envelope, which is derived from the cell that the virus infects, when the virus buds from the cell as a mature virion. These mature virions recognize some components of a cell to allow attachment before the genetic material is injected into the cell. For example, COVID-19 uses the ACE-2 protein in the membrane to initiate a binding event. After the initial binding event, the viral genetic material is deposited inside the cell where it begins its replication process. MFG also contain the ACE-2 protein from the mammary cells from which the globules were created. When MFG are present and one contacts an enveloped free virus, such as the COVID-19 coronavirus, the virus can bind to the milk fat globule. MFG are effectively fat molecules with no genetic material. Thus, when a virus binds with a milk fat globule, the virus releases its RNA into the milk fat globule rendering the virus non-infectious. While such interactions do not amount to a cure for the virus, they do reduce the infectivity of people who have the virus. One reason is because droplets expelled from the mouth of the infected person no longer contain infectious COVID-19. Another reason why such interactions reduce the infectivity of people who have the virus is because, if ingested, the virus is tied up in a digestion pathway and with no way to replicate.

In an example, a person infected with the COVID-19 coronavirus can be treated with MFG, for example, generated according to the methods described herein. The MFG contact the free form of the enveloped COVID-19 coronavirus, and the COVID-19 coronavirus binds to the milk fat globule. When the COVID-19 coronavirus binds with the milk fat globule, the COVID-19 coronavirus releases its RNA into the MFG milk fat globule, rendering the COVID-19 coronavirus non-infectious.

Herpes simplex virus type-1 (HSV-1) and Herpes simplex virus type-2 (HSV-2), as well as Herpes Zoster virus (HZV), are highly prevalent human pathogens causing life-long infections. The process of infection begins when the virions bind with heparan sulfate moieties present on host cell surfaces. This initial attachment then triggers a cascade of molecular interactions involving multiple viral and host cell proteins and receptors, leading to penetration of the viral nucleocapsid and tegument proteins into the cytoplasm. The nucleocapsid is then transported to the nuclear membrane and the viral DNA is released for replication in the nucleus. Recent studies have revealed that HSV entry or penetration into cells may be a highly complex process and the mechanism of entry may demonstrate unique cell-type specificities. While specificities clearly exist, some past and ongoing studies also demonstrate that HSV may share certain common receptors and pathways also used by many other human viruses.

According to the present invention, MFG, that obtain their membrane from mammary cells, are used to treat HSV-1, HSV-2, HZV, and the like. The MFG contain the components associated with the initial interaction between the viral coat and the cell membrane. The cell surface proteoglycans on normal mammary epithelial cells consists of an ectodomain bearing heparan and chondroitin sulfate chains and a lipophilic domain that is presumed to be intercalated into the plasma membrane. The interaction between a virus and the MFG leads to injection of the virus' genetic material into the milk fat globule, rendering the virus particle noninfectious. Such treatment, including, for example, administering dosages of MFG to an infected patient, can be carried out with or without the use of additional anti-viral agents.

According to various embodiments, a composition such as an anti-viral agent is provided that comprises MFG with or without an encapsulated anti-viral agent, wherein the MFG is from non-homogenized or homogenized milk. The agent can be combined with a pharmaceutically acceptable carrier. The agent can be used to reduce the infectivity of COVID-19 and other enveloped viruses. The composition or anti-viral agent can comprise MFG that have been machine-manipulated to encapsulate a therapeutic agent. The MFG can be sourced from cream that has been separated from milk. The MFG can be sourced from a liquid cream effluent resulting from a centrifugation of milk. The therapeutic agent can be packaged in a bottle. A method of making a composition, for example, an anti-viral composition, as described herein, is also provided. The MFG can be from a non-homogenized source and the method can comprise machine-manipulating the MFG. The method can use MFG comprising homogenized cream effluent, and the method can comprise machine-manipulating the MFG to form a machine-manipulated MFG. The method can further comprise reducing the machine-manipulated MFG to a powder. Reducing the machine-manipulated MFG to a powder can comprise freeze-drying the machine-manipulated MFG.

According to various embodiments, a method of inactivating an enveloped virus is provided that comprises mixing MFG with cannabinoids to form an inactivating agent. The agent can be used against enveloped viruses. The method can involve administering the inactivating agent to a patient infected with an enveloped virus. The agent can be an ointment or a spray and the cannabinoids can comprise full-spectrum hemp oil. The method can further comprise reducing the inactivating agent to a powder. The cannabinoids can comprise naturally occurring molecules that are purified from hemp, *cannabis*, or other plant sources. The method can involve synthetically preparing the cannabinoids prior to mixing with the MFG. The cannabinoids can be sourced from genetically engineered microorganisms grown in a controlled environment. The cannabinoids can be obtained from genetically engineered plants grown in a field or greenhouse. The cannabinoids can be first obtained from plant cell cultures.

According to various embodiments, a composition is provided that comprises MFG mixed with a hydrophilic anti-viral agent. The anti-viral agent can comprise a natural substance. The anti-viral agent can comprise a synthesized chemical compound. The anti-viral agent can be genetically engineered.

According to various embodiments, a composition is provided that comprises MFG mixed with a hydrophobic anti-viral agent. The anti-viral agent can comprise a natural substance. The anti-viral agent can comprise a synthesized chemical compound. The anti-viral agent can be genetically engineered.

According to various embodiments, a composition is provided that comprises a pharmaceutically acceptable topical carrier and a composition that comprises an anti-viral agent, a sunscreen agent, or both, encapsulated in MFG. The pharmaceutically acceptable topical carrier can comprise an oil. The pharmaceutically acceptable topical carrier can comprise a cream. The pharmaceutically acceptable topical carrier can comprise a lotion. The pharmaceutically acceptable topical carrier can comprise a butter. The pharmaceutically acceptable topical carrier can comprise a spray. The pharmaceutically acceptable topical carrier can comprise a pressurized spray composition contained in a pressurized container. The pharmaceutically acceptable topical carrier can comprise a gargle for oral use. The pharmaceutically acceptable topical carrier can comprise an ophthalmic solution for use in an eye. The pharmaceutically acceptable topical carrier can comprise a lavage for vaginal use. The composition can be a therapeutic composition.

According to various embodiments, a capsule, tablet, or combination thereof, is provided that comprises MFG and a pharmaceutically acceptable carrier for internal use. The composition can comprise MFG and melanin, and the melanin can be encapsulated in the MFG. The composition can comprise a pharmaceutically acceptable topical carrier. The melanin can comprise Eumelanin. The eumelanin can comprise eumelanin isolated from natural sources. The eumelanin can comprise eumelanin synthesized from a synthetic source. The melanin can be pheomelanin. The pheomelanin can comprise pheomelanin isolated from natural sources. The pheomelanin can comprise pheomelanin produced from a synthetic source.

According to various embodiments, a composition is provided that comprises MFG, melanin, and an antioxidant, wherein the melanin and the antioxidant can be encapsulated in the MFG. The antioxidant can comprise full spectrum hemp oil obtained from harvesting in fields, green houses, fermentation vessels, or plant cell culture. The antioxidant can comprise broad spectrum hemp oil, CBD, purified CBD, or the like. The composition can further comprise a pharmaceutically acceptable topical carrier. The pharmaceutically acceptable topical carrier can comprise an oil. The pharmaceutically acceptable topical carrier can comprise a cream. The pharmaceutically acceptable topical carrier can comprise a lotion. The pharmaceutically acceptable topical carrier can comprise a butter. The pharmaceutical carrier for topical application can comprise a spray. The pharmaceutical carrier for topical application can comprise a pressurized spray composition contained in a pressurized container.

According to various embodiments, an anti-aging composition is provided that comprise MFG and one or members selected from the group consisting of retinols, vitamin E, tocopherols, and tocotrienols, wherein the one or more members are encapsulated in the MFG. The retinols, vitamin E, tocopherol, and tocotrienols can be independently be derived from natural sources. The retinols, vitamin E, tocopherol, and tocotrienols can independently be derived from synthetic sources. The retinols, vitamin E, tocopherol, and tocotrienols can independently be derived from genetically engineered sources. The anti-aging composition can further comprise a pharmaceutically acceptable carrier and can be formulated to be delivered orally, topically, or both. The pharmaceutically acceptable carrier can comprise an oil. The pharmaceutically acceptable carrier can comprise a cream. The pharmaceutically acceptable carrier can comprise a lotion. The pharmaceutically acceptable carrier can comprise a butter. The pharmaceutically acceptable carrier can comprise a pressurized spray composition contained in a pressurized container. The pharmaceutically acceptable carrier can comprise a spray composition and the anti-aging composition can be contained in a container that comprises a spray nozzle.

According to various embodiments, a composition is provided that comprises MFG and modified eumelanin, wherein the modified eumelanin can be encapsulated in the MFG.

The composition can further comprise a pharmaceutically acceptable carrier and can be formulated to be delivered orally, topically, or both. The pharmaceutically acceptable carrier can comprise an oil. The pharmaceutically acceptable carrier can comprise a cream. The pharmaceutically acceptable carrier can comprise a lotion. The pharmaceutically acceptable carrier can comprise a butter. The pharmaceutically acceptable carrier can comprise a pressurized spray composition contained in a pressurized container. The pharmaceutically acceptable carrier can comprise a spray composition and the spray composition can be contained in a container that comprises a spray nozzle.

According to various embodiments of the present invention, a method for treating a systemic infection caused by an enveloped virus is provided. The method comprises gargling with a gargle composition, wherein the gargle composition comprises from 1% by weight to 80% by weight milk fat globules obtained from a mammalian source. The gargle composition can contain a liquid carrier. The gargling can be carried out at least twice over a two-day period, over a three-day period, over a four-day period, over a five-day period, over a seven-day period, over a 10-day period, or over a 12-day period. The gargling can be carried out at least twice per day, for at least three days, for at least four days, for at least five days, for at least seven days, for at least ten days, or for at least twelve days. The gargling can be carried out once per day, at least twice per day, at least three times per day, at least four times per day, or for at least five times per day.

The method can further comprise testing a patient for a systemic infection caused by an enveloped virus, determining from the testing that the patient is systemically infected with an enveloped virus, and administering to the patient, the gargling, for example, immediately, within 1 hour of the determining, within 6 hours of the determining, within 12 hours of the determining, within 24 hours of the determining, within three days of the determining, or within five days of the determining, or within two weeks of the determining. The enveloped virus treated can be the COVID-19 coronavirus.

The method can further comprise preparing the gargle composition. The preparing can comprise mixing powered milk fat with the liquid carrier to form the gargle composition. A patient's oropharyngeal cavity can be treated accordingly, or by administering the gargle composition as a throat spray, for example, through a pump spray bottle. The method can involve gargling with the gargle composition for at least three seconds, and expelling the gargle composition after the gargling.

The method can comprise testing a human for the COVID-19 coronavirus. The method can comprise determining, from testing a human for the COVID-19 coronavirus, that the human is infected with the COVID-19 coronavirus. The method can involve administering the gargling to the human, providing the human with the gargle composition as described herein, presenting the gargle solution to the patient, or the like, within three days of determining, from testing a human for the COVID-19 coronavirus, that the human is infected with the COVID-19 coronavirus.

A method for treating a topical infection caused by an enveloped virus, is provided. The method can comprise applying, to the topical infection, an antiviral composition comprising milk fat globules obtained from a mammalian source. The antiviral composition can comprise, for example, from 5% by weight to 100% by weight milk fat globules, from 5% by weight to 80% by weight milk fat globules, from 5% by weight to 65% by weight milk fat globules, from 10% by weight to 100% by weight milk fat globules, from 25% by weight to 100% by weight milk fat globules, from 30% by weight to 90% by weight milk fat globules, from 40% by weight to 80% by weight milk fat globules, from 50% by weight to 70% by weight milk fat globules, or from 61% by weight to 90% by weight milk fat globules, based on the total weight of the antiviral composition. The antiviral composition can comprise a pharmaceutically acceptable carrier, for example, making up the balance of the composition. The pharmaceutically acceptable carrier can comprise petrolatum, paraben, mineral oil, aloe, shea butter, hemp oil, full spectrum hemp oil, broad spectrum hemp oil, CBD, purified CBD, full spectrum hemp oil with CBDA/CBD at about a 1:1 ratio, coconut oil, beeswax, cocoa butter, vitamin A, vitamin D, vitamin E, oil blends, combinations thereof, and the like. The pharmaceutically acceptable carrier can comprise oil blends including blends of two or more of almond oil, argan oil, avocado oil, coconut oil, moringa oil, jojoba oil, and hempseed oil. The pharmaceutically acceptable carrier can comprise powder and essential oil drops.

Inert propellants can be included, for example, $CO_2$, $N_2$, clean dry air, saline spray, and the like. Pharmaceutical grade propellants such as isobutane can also be used. The composition can be provided as an ointment, a spray, a salve, a lotion, a cream, a butter, or the like. The pharmaceutically acceptable carrier can comprise micelles, vesicles, liquid crystals, nano capsules, nanospheres, multifunctional dendritic polymers, combinations thereof, and the like.

The antiviral composition can comprise from 10% by weight to 95% by weight milk fat globules obtained from a mammalian source, based on the total weight of the antiviral composition. The antiviral composition can comprise from 5% by weight to 90% by weight the pharmaceutically acceptable carrier. The antiviral composition can be in the form of a lip balm. The pharmaceutically acceptable carrier can comprise petrolatum. The topical infection can be an infection on the lips. The method can comprise applying a lip balm as described herein, to a topical infection on the lips.

The antiviral composition can be in the form of a spray. The method can comprise spraying the antiviral composition on a topical infection. The antiviral composition can comprise a salve and the method can comprise applying the salve to the topical infection. The topical infection can be one caused by one or more viruses selected from the group consisting of Herpesviruses, Poxviruses, Hepadnaviruses, Asfarviridae, RNA viruses, Flavivirus, Alphavirus, Togavirus, Coronavirus, Hepatitis D, Orthomyxovirus, Paramyxovirus, Rhabdovirus, Bunyavirus, Filovirus, and Retroviruses. Other enveloped virus infections can also be treated according to embodiments of the present invention.

According to various embodiments, a packaged gargle composition is provided. The packaged gargle composition can comprise a container and a gargle composition contained in the container. The gargle composition can comprise milk fat globules, for example, up to 100% by weight milk fat globules from a mammalian source, based on the total weight of the gargle composition. The container can comprise directions for use thereon, and the directions for use can include directions for gargling. The directions for use can include directions for expelling after gargling. The directions for use can include directions for swallowing after gargling.

The gargle composition can comprise from 1% by weight to 80% by weight milk fat globules obtained from a mammalian source, based on the total weight of the gargle composition, and a liquid carrier. The liquid carrier can be edible, ingestible, inedible, flavored, or a combination thereof. The liquid carrier can comprise one or more of water, milk, fruit juice, a sugar solution, a sports drink, tea, chilled coffee, a mouth wash, an ethanol-based liquid, a liquor, a beer, an ale, spirits, an electrolytes solution, combinations thereof, and the like. The liquid carrier can be packaged with liquid or powdered milk fat globules, packaged separately, or not packaged at all with the milk fat globules.

The packaged gargle composition can contain a gargle composition that comprises powdered milk fat globules. The directions for use can further include directions for making a gargle composition by mixing a liquid with the powdered milk fat globules. The container for the packaged gargle composition can comprises a plurality of inner containers contained therein, for example, small bottles containing liquid gargle composition, packets or envelopes containing powdered gargle composition, single use containers containing single dosages of gargle composition, combinations thereof, and the like.

An antiviral composition is provided that comprises milk fat globules obtained from a mammalian source, and a pharmaceutically acceptable topical carrier. The antiviral composition can comprise from 5% by weight to 95% by weight milk fat globules, based on the total weight of the antiviral composition, and the pharmaceutically acceptable topical carrier can comprise one or more carriers selected from the group consisting of petrolatum, paraben, mineral oil, aloe, shea butter, hemp oil, full spectrum hemp oil, broad spectrum hemp oil, CBD, purified CBD, full spectrum hemp oil with CBDA/CBD at a 1:1 ratio, coconut oil, beeswax, cocoa butter, an oil blend, almond oil, argan oil, avocado oil, coconut oil, moringa oil, jojoba oil, hempseed oil, and combinations thereof. The antiviral composition can comprise from 5% by weight to 95% by weight milk fat globules, based on the total weight of the antiviral composition, and the pharmaceutically acceptable topical carrier can comprise one or more carriers selected from the group consisting of micelles, vesicles, liquid crystals, nano capsules, nanospheres, and multifunctional dendritic polymers.

The antiviral composition can comprise from 10% by weight to 95% by weight milk fat globules from a mammalian source, based on the total weight of the antiviral composition, and from 5% by weight to 90% by weight the pharmaceutically acceptable topical carrier. The antiviral composition can comprise from 15% by weight to 85% by weight milk fat globules from a mammalian source, based on the total weight of the antiviral composition, and from 15% by weight to 85% by weight the pharmaceutically acceptable topical carrier. The antiviral composition can comprise from 25% by weight to 75% by weight milk fat globules from a mammalian source, based on the total weight of the antiviral composition, and from 25% by weight to 75% by weight the pharmaceutically acceptable topical carrier. The antiviral composition can comprise from 40% by weight to 60% by weight milk fat globules from a mammalian source, based on the total weight of the antiviral composition, and from 60% by weight to 40% by weight the pharmaceutically acceptable topical carrier.

The antiviral composition can be in the form of a lip balm, for example, contained in a tube, a twist tube, a jar, a metal tube, a plastic tube, or the like. The antiviral composition can be in the form of a sprayable liquid. The antiviral composition can be contained in a container that has a spray nozzle. The antiviral composition can be contained in a pump-spray container. The antiviral composition can be contained in a pressurized spray container. The antiviral composition can be in the form of a salve. The antiviral composition can be in the form of a salve and the salve can be contained in a tube, for example, a deformable metal tube or a deformable plastic tube. The antiviral composition can be in the form of a salve and the salve can be contained in a jar.

According to various embodiments, treating a patient with an active COVID-19 infection involves adding the MFG to the mouth where the active virus is found. This is accomplished by gargling a solution containing MFG with or without an anti-viral. For example, the solution can contain 12% non-homogenized MFG and 6% full spectrum hemp oil. One ounce of this solution can be gargled 3× to 4× a day during the active stage of the infection. The material can be swallowed delivering both the inactive virus and the full spectrum hemp oil to the stomach. Alternatively, the patient can spit out the material. In the case of Herpes virus infection, it depends upon the infected area.

With Herpes zoster, for example, the virus replicates at nerve endings on or near the skin forming blisters, itching and pain. In this case, an ointment can be used to treat the affected areas. A salve containing 2 parts coconut oil, 1 part beeswax, 2 parts shea butter, 2 parts cocoa butter, 1 part of 8% full spectrum hemp oil with CBDA/CBD at about a 1:1 ratio and 0.1 part of vitamins A, D and E is applied to the skin once the 'red blotches' emerge 3× a day for 10 days. This prevents the formation of blisters and scabbing as well as the inflammation and itching generally associated with the red blotches.

For Herpes simplex fever blister on the lips, a lip balm, containing 1 part cocoa butter, 1 part 7 oil blend (almond, argan avocado, coconut, moringa, jojoba, hempseed), 1 part beeswax, 1 part 10% powder and 0.1 part of essential oil drops, is applied to the lips 3× to 4× a day or as needed. For genital Herpes, a patient can use a salve such as the one used for shingles or in the lip balm. Alternatively, MFG with 10% full spectrum oil can be added to a pump spray. Alternatively, the spray can is packaged under pressure similar to that used for saline nasal spray. Inert propellants, such as, $CO_2$ or $N_2$ are preferred but pharmaceutical grade propellants such as isobutane can also be used. The material, either the ointment or the spray, can be applied 3× to 4× a day.

Treatment of Epstein Barr Virus (EBV) infections, such as mononucleosis, are similar to treating COVID-19. That is, the oropharyngeal cavity is the source of transmitting the EBV to another person. Therefore, treating the saliva with a protocol similar to COVID-19 would work to inactivate EBV. For example, the solution can contain 12% non-homogenized MFG and 6% full spectrum hemp oil. One ounce of this solution can be gargled 3× to 4× a day during the active stage of the EBV infection which generally last several weeks.

For sunscreen and anti-aging compositions, one or more of the pharmaceutically acceptable topical carriers described herein can be included in the compositions.

Sunscreen and Pyrimidine Dimers

The absorbed energy from the sun can be used to form covalent bonds between adjacent pyrimidines in the DNA. Generally, the DNA repair systems in the cells monitor the DNA and repair the damage by removing the dimers.

However, if these dimers are not repaired prior to replication, they introduce mutations into the DNA and change the cell. A consequence of these mutagenic events may be manifested in basal cell carcinoma, squamous cell carcinoma, or melanomas.

Reactive Oxygen Species (ROS)

Figure 4:
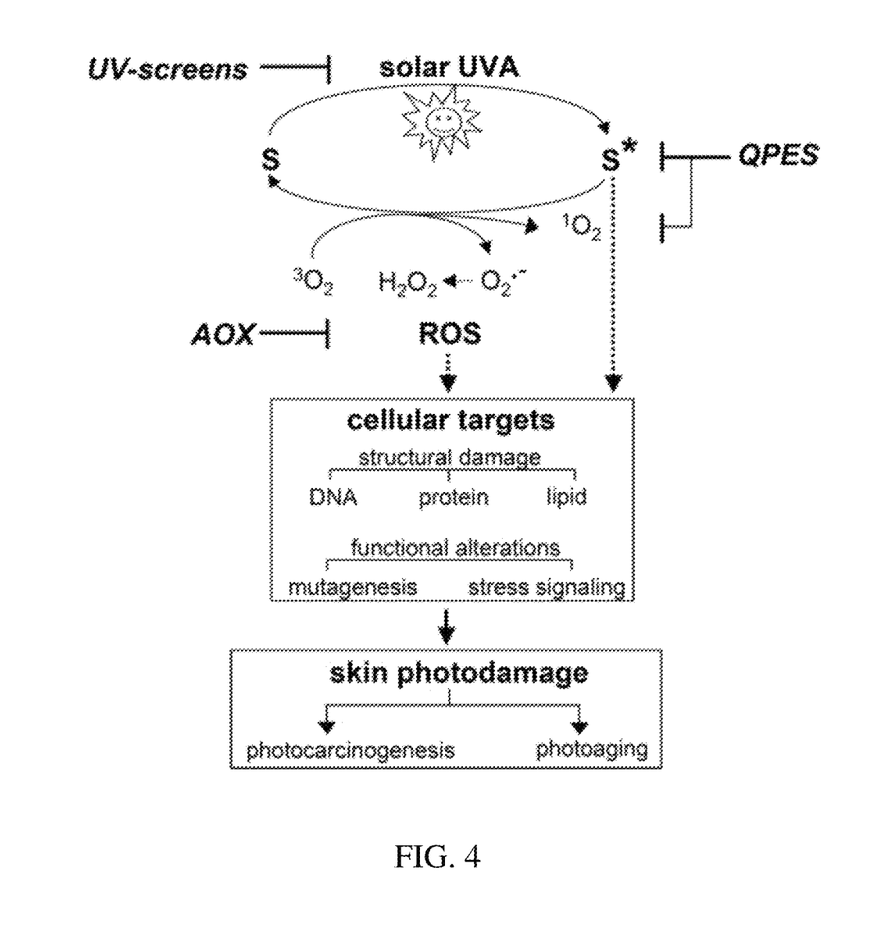

While the body can eliminate these potentially toxic chemicals, there is a limit to its ability to do so. Thus, substantial biological and biochemical events can occur if the ROS are not eliminated. Random cellular damage and the initiation of specific signaling pathways can create metabolic dysfunction. This is diagrammatically illustrated in FIG. 4, taken from Wondrak et al. (2005, J. PHARM. EXPTL THER. 312:482-419).

APES For Skin Photoprotection

Exposure of human skin to solar UVA radiation induces the formation of photoexcited states (S*) of endogenous skin chromophores (S). Some photoexcited chromophores act as toxic photosensitizers by direct chemical interaction with cellular target molecules or by interaction with oxygen leading to the formation of ROS. Energy transfer from S* to molecular oxygen induces the formation of photoexcited oxygen ($^1O_2$), being both a ROS and a photoexcited state species. Molecular damage inflicted by ROS and S* on cellular targets in skin, leading to mutagenesis and altered signal transduction, contribute ultimately to photocarcinogenesis and photoaging of skin. UV screens only partly absorb solar broad-spectrum UVA radiation. Antioxidants (AOX) are the direct molecular antagonists of ROS. There is a need to quench the photoexcited state. Quenchers of the photoexcited state (QPES), are used for this purpose. QPES are the molecular antagonists of skin photoexcited states acting upstream of antioxidant intervention.

The ability of cells to quench the photoexcited state represents one way that the potentially harmful UV rays are alleviated. When ROS are generated however, the next line of defense is the antioxidants in the cell. These molecules convert the potentially dangerous oxygen reactive species to normal cellular components thus avoiding any damage that might be caused by these molecules.

According to various embodiments of the present invention, a topical ointment is provided for a sunscreen, which provides chemicals that can reduce the ramifications of potentially dangerous UV rays.

Figure 5:
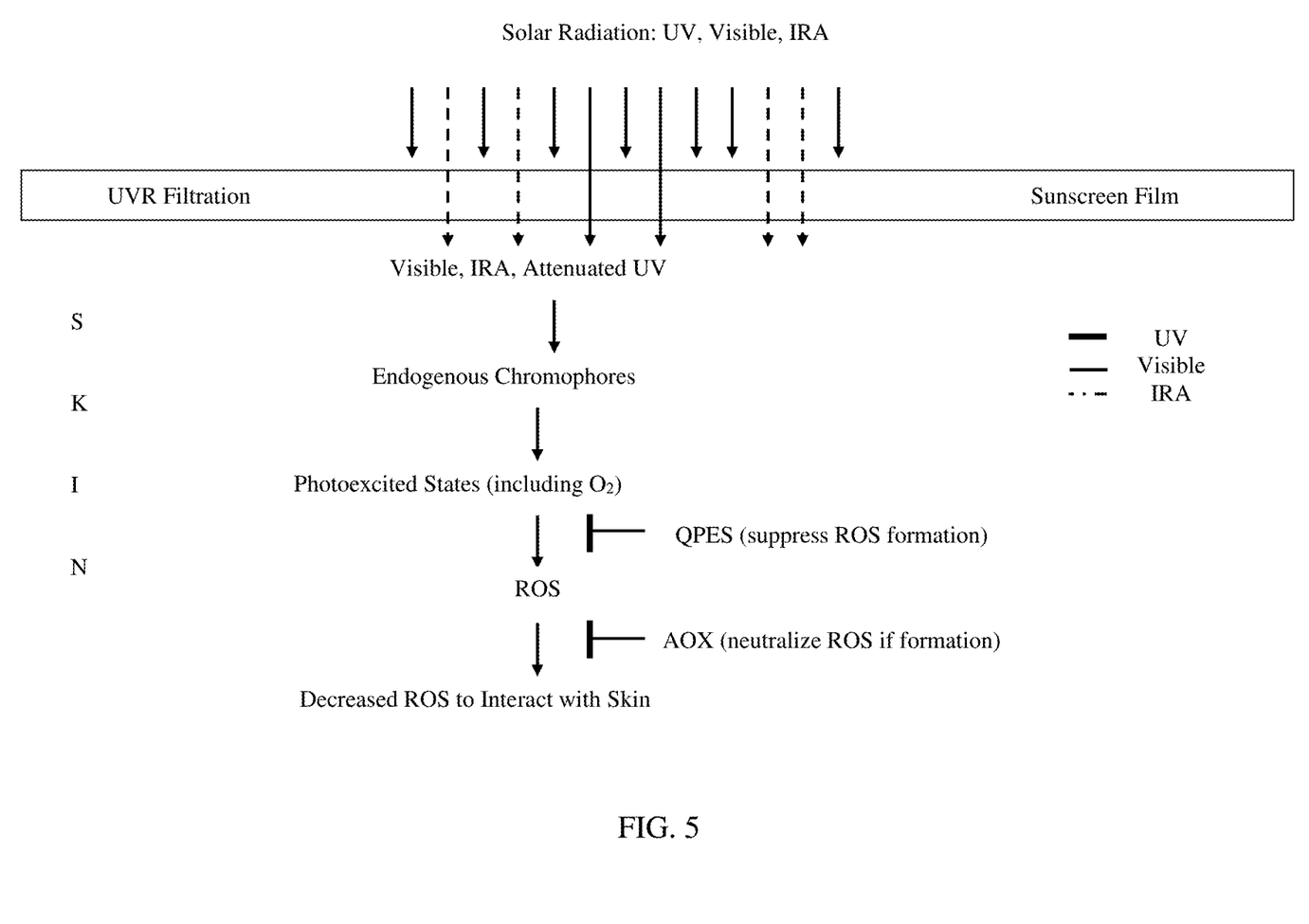

FIG. 5 is a schematic illustration showing the abilities of sunscreens, quenchers of photoexcited states (QPES), and antioxidants (AOX), to suppress formation of or scavenge of reactive oxygen species (ROS) in human skin. FIG. 5 schematically illustrates the complimentary action of sunscreens, quenchers of photoexcited states (QPES), and antioxidants (AOX). Sunscreens attenuate UV before it can interact with endogenous chromophores of the skin, while QPES relax photoexcited states before they can sensitize ROS formation, and AOX neutralize ROS if formed. The action of all three ingredients functions to decrease the extra burden of ROS formed within skin during exposure to solar radiation.

A striking feature that can be discerned from FIG. 5 is how well these three ingredients is appear to complement one another to suppress formation or scavenge of ROS within skin. Sunscreens filter the sun's UV radiation at the skin's surface to attenuate levels of UVR that can reach and interact with endogenous chromophores in the underlying skin, whereas QPES and AOX each work within skin below the protective sunscreen film. QPES function upstream of ROS formation by relaxing photoexcited states via electron transfer or energy transfer pathways before they can sensitize the formation of ROS. Antioxidants, on the other hand, scavenge ROS once formed before they can initiate damaging radical interactions with skin.

According to embodiments of the present invention, a sunscreen is provided that limits the number of UV rays passing through the skin and also, for UV rays that have passed through the epidermis, provides a means to dissipate the absorbed energy. The following are exemplary components:

Avobenzone 2.7%

Avobenzone is a dibenzoylmethane derivative which in the ground state is a mixture of the enol and keto forms. This enol form, which is stabilized by intramolecular hydrogen-bonding, absorbs ultraviolet light over a range of wavelengths allowing its use in "broad spectrum" sunscreens. Avobenzone has an absorption maximum of 357 nm.

Homosalate 4%

Homosalate is an organic compound used in 45% of U.S. sunscreens as a chemical UV filter. The salicylic acid portion of the molecule absorbs ultraviolet rays from 295 nm to 315 nm, thus protecting the skin from sun damage.

Octisalate 4.5%

Octyl salicylate, or 2-ethylhexyl salicylate, is an organic compound used as an ingredient in sunscreens and cosmetics to absorb UVB (ultraviolet) rays from the sun. The salicylate portion of the molecule absorbs ultraviolet light. The ethylhexanol portion is a fatty alcohol, adding emollient and oil-like (water resistant) properties.

Octocrylene 6%

Octocrylene is an organic compound used as an ingredient in sunscreens and cosmetics. It's a clear, colorless, viscous, oily liquid. The molecule absorbs both UVB and short-wave UVA (280 to 320 nm), protecting the skin from direct DNA damage. Octocrylene is a fatty alcohol, adding emollient and oil-like (water resistant) properties, and can penetrate into the skin. However, it acts as a photosensitizer resulting in an increased production of free radicals under illumination.

Oxybenzone 4.5%

Oxybenzone absorbs light at lower energies than many aromatic molecules. As a sunscreen, it provides broad-spectrum ultraviolet coverage, including UVB and short-wave UVA rays. It is one of the most widely used organic UVA filters in sunscreens today.

The sunscreen can provide a base that absorbs UV rays thereby filtering the energy reaching the skin. The present invention also provides a sunscreen that provides an agent that can neutralize ROS that could be generated by the UV rays that are not absorbed by this sunscreen. The present invention provides a method that uses MFG as a base for sunscreen formulations. The MFG can be combined with at least 2 components: melanin and an antioxidant, such as full spectrum hemp oil. The melanin provides for the absorption of UV rays over a broad spectrum, while the antioxidant reduces the formation of ROS. In another embodiment, some or all the chemical fat-soluble sunscreen components can be combined with the MFG and formulated as a sunscreen.

Eumelanin

The physical and chemical nature of melanin makes it a key component of the human pigmentary system. The degree of pigmentation of the human skin, hair and eyes is, to a large extent, determined by the ability of specialized cells to synthesize the brown-black eumelanin and yellow-reddish pheomelanin. Eumelanin is commonly accepted to be a heterogeneous macromolecule of 5,6-dihydroxyindole (DHI) and its 2-carboxylated form 5,6-dihydroxyindole2-carboxylic acid (DHICA). Pheomelanin is derived from the sulphur containing cysteinyldopa (CD), and again is thought to be heterogeneous macromolecule.

The function of melanin is defined by their physical and chemical properties. These properties, including features such as anti-oxidant and free-radical scavenging behavior, broad band UV and visible absorption and strong non-radiative relaxation of photo-excited electronic states, are defined by the molecular, supramolecular and aggregate-level structure.

The remarkable ability of both eumelanin and pheomelanin to absorb photons from the ultraviolet and visible parts of the solar spectrum, may explain, in part, the photochemistry of this pigment. Due to very fast photodynamics of eumelanin in particular, which is responsible for almost complete conversion of the energy of the absorbed photons into heat, very few excited melanin molecules have a chance to participate in photochemical reactions.

Melanin in the skin and eye acts as a natural sunscreen by absorbing and scattering solar radiation, particularly the energetic UV and short wavelength visible photons, and protects pigmented tissue against adverse photo-reactions. A distinct correlation between the resistance of the human skin to UV-induced erythema and sunburn, and constitutive pigmentation of the skin is usually observed.

The ability of melanin to quench excited states of photosensitizing dye molecules and singlet oxygen, and scavenge reactive radicals is an important factor in protective action of melanin against oxidative damage that in pigmented tissues could be induced by photochemical or chemical processes. The mechanism of quenching of excited states of positively charged porphyrin dye molecules bound to melanin was recently determined by femto-second absorption and pico-second emission spectroscopies. It has been concluded that such an ionic binding facilitates an ultrafast energy transfer from the excited porphyrin molecule to melanin. The excited energy is then rapidly converted into heat. Because of its speed, the process involves only singlet excited states; no triplet states are formed and, consequently, no photochemistry occurs.

Photoacoustic spectroscopy shows that melanin photodynamics is very rapid and the excited energy is efficiently converted into heat.

Eumelanin represents a unique way to dissipate the absorbed UV rays thus providing superior protection against UV rays of all types. That action combined with the ability of eumelanin to serve as a QPES agent as well as an antioxidant makes this a unique component of the sunscreen.

Antioxidants

While the melanin can dissipate most of the energy from the UV rays, it is possible that some ROS could be generated. Therefore, it makes sense to include some compounds that serve as antioxidants without being photosensitizing agents. Some examples of antioxidants include: Vitamin E; Vitamin C; Cannabinoids of hemp oil; Glutathione; Vitamin D; Melatonin; Carotenoids; Flavonoids; Uric acid; Selenium; Resveratrol; Curcumin.

Antiaging

There are data suggesting the tocotrienols are safe members of the vitamin E family that have positive biochemical effects. Vitamin E family members, tocotrienols and tocopherols, are widely known for their health benefits. Decades of research on tocotrienols have shown they have diverse biological activities such as antioxidant, anti-inflammatory, anticancer, neuroprotective and skin protection benefits, as well as improved cognition, bone health, longevity and reduction of cholesterol levels in plasma. Tocotrienols also modulate several intracellular molecular targets and, most importantly, have been shown to improve lipid profiles, reduce total cholesterol and reduce the volume of white matter lesions in human clinical trials. This review provides a comprehensive update on the little-known therapeutic potentials of tocotrienols, which tocopherols lack in a variety of inflammation-driven diseases.

These molecules are lipid soluble, and because they are, they work well with the MFG as a carrier and can be delivered either externally or internally using the same basic formulation.

Retinoids have also been reported to help with age related changes to the skin. Similarly, many of the physiological responses of the skin, such as dermal aging, immune defense, and wound healing, are significantly affected by retinoids. A balance between synthesis and enzymatic degradation of extracellular matrix proteins is required for homeostasis in the dermis. In aging skin, the synthesis of matrix proteins slows. These biochemical changes in the dermis can result in the sagging and wrinkles commonly observed in aged skin. Chronic exposure to sunlight can further exacerbate these biochemical changes in the dermis. In humans, retinyl esters (mostly retinyl palmitate) in chylomicrons may predominate in the blood for 3-6 h following ingestion of a retinol-rich meal.

Figure 6:
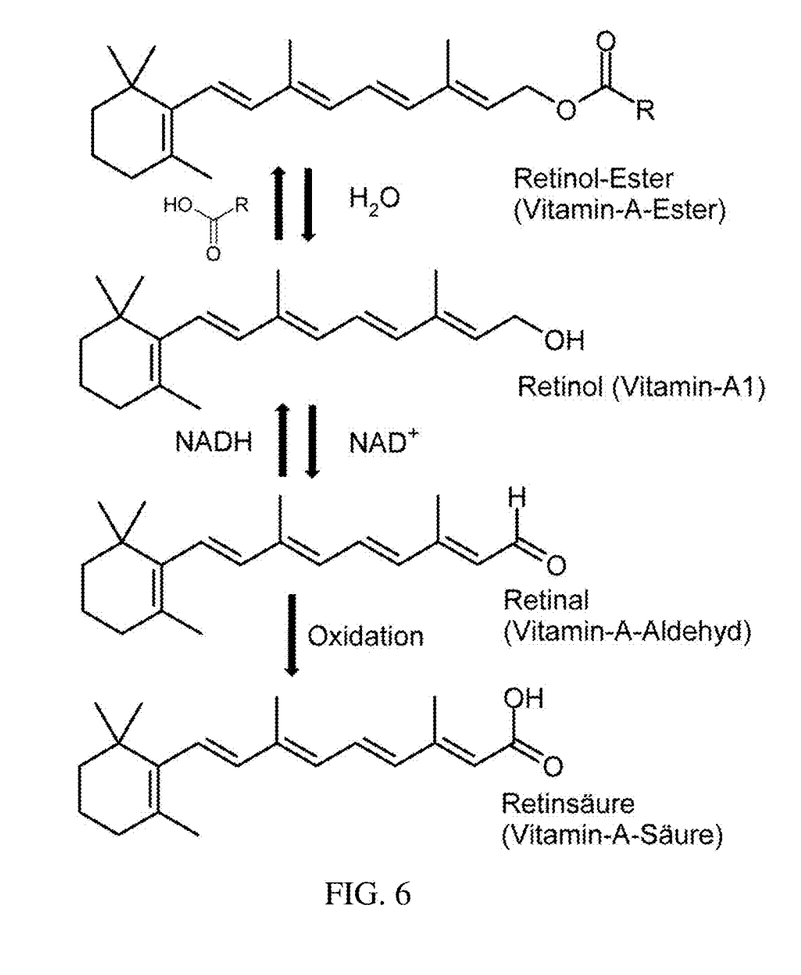

Retinoids, that have the structures shown in FIG. 6, can be formulated with MFG to create a pathway that enables an improved absorption of vitamin A. In various embodiments, retinoids, such as those shown in FIG. 6, can be formulated with MFG and delivered to the skin of a patient, in a formulation that enables the absorption of these molecules into the skin.

In various embodiments, in vitro experimenting and/or testing can be carried out to analyze the ability of MFG to inactivate, or render ineffective, an enveloped virus such as the COVID-19 coronavirus, many Herpes viruses, the Epstein Barr virus, and the like. In a laboratory, for example, in a petri dish, cell-culture plate, or other laboratory vessel, MFG can be brought into contact with an enveloped virus to test the efficacy of the MFG in acting as surrogate cells to bind to the virus. By binding to a milk fat globule, the virus cannot then bind to a cell of a host organism. Successful in-vitro trials can be used to select candidate viruses and milk fat globule structures that can effectively bind together to prevent further replication of the bound virus.

Examples

While MFG can come from different sources, for example, raw milk or pasteurized milk, either of which can be homogenized or non-homogenized, MFG is used herein as a representative of those structures.

Source of MFG:
  Milk—3-4%
  Half and half—10-18%
  Light cream—16-29%
  Heavy cream—33-39%
  Heavy cream powder—63-70%

Test virus for Experiments 1-3:
  HSV-1—Herpes Simplex type 1
  Experiment 1
  1. Titer a stock solution of HSV-1.
  2. Add the MFG from various sources to an aliquot of HSV-1
  3. Incubate at room temperature or 37° C. for 10-60 minutes.
  4. Separate the HSV-1 from the MFG by filtration.

5. Titer the virus to see if the incubation with the MFG reduced the level of infective HSV 6. Treat the MFG with an agent from plants, for example, curcumin or hemp oil and repeat.

Experiment 2

1. Titer a stock solution of HSV-1.
2. Treat MFG with full spectrum hemp oil to achieve curcumin or cannabinoid concentrations of:
   a. 5 mg/ml
   b. 10 mg/ml
   c. 20 mg/ml
   d. 50 mg/ml
3. Add MFG from various sources containing full spectrum hemp oil, to an aliquot of HSV-1.
4. Incubate at room temperature or 370 C for 10-60 minutes.
5. Separate the HSV-1 from the MFG by filtration.
6. Titer the virus to see if the incubation with the MFG reduced the level of infective HSV-1.
7. Treat the MFG with THC-free broad-spectrum hemp oil.

Experiment 3

1. Titer a stock solution of HSV-1.
2. Treat MFG with full spectrum hemp oil to achieve cannabinoid concentrations of:
   a. 5 mg/ml
   b. 10 mg/ml
   c. 20 mg/ml
   d. 50 mg/ml
3. Add MFG from various sources containing full spectrum hemp oil, to an aliquot of HSV-1.
4. Incubate at room temperature or 370 C for 10-60 minutes.
5. Separate the HSV-1 from the MFG by filtration.
6. Titer the virus to see if the incubation with the MFG reduced the level of infective HSV-1.

Experiment 4—Treating Shingles

Day 1, A patient noticed a red itchy rash on the right side of his chest and shoulder with a few red blotches on his neck and upper back. There were also 3 small blisters at the base of his neck. He assumed it was shingles, but to be sure, he had a teleconference with a personal physician. The physician confirmed the patient's suspicion and prescribed 21 capsules of valacyclovir, an antiviral compound.

A 10-gram mixture aliquot was taken after being prepared from a mixture of: 2 ounces of seven oil blend; 1 ounce of coconut oil; 1 ounce of beeswax; 2 ounces of shea butter; 2 ounces of cocoa butter; and 1 ounce of 4% powder. Then, 10 grams of 10% CBDA/CBD milk fat globule powder was added to the 10-gram mixture aliquot and the 10% CBDA/CBD milk fat globule powder was mixed into the mixture aliquot to form an ointment having a uniform tan appearance. The patient applied the ointment in the morning and continued applying the ointment 3 times that day. The itching, which was about a 2-3 on a 10-point scale, subsided about 5-10 minutes after applying the ointment, and did not occur again that day. At about 4:00 PM, the patient took his first tablet of valacyclovir and continued taking them every 8 hours for the next 7 days.

The patient continued applying the ointment in the morning and evening of each day. After a week, the red blotches were slightly less raised and red. There was no pain or itching and no new blisters developed during the week. The original 3 small blisters disappeared with no evidence of bursting or scabbing.

On day seven, the patient decided not to put the ointment on in the morning. By the evening there was some itching so the patient applied some of the ointment. There were no blisters or scabs, but the patient could still see the red blotches.

On day eight, the patient put the ointment on in the morning and made a new batch of ointment. On day ten, the red blotches were clearly subsiding. On day 13, the red blotches were fading even more and there still was no scabbing or itching. On day 15, there was little evidence of the red blotches.

It was concluded that the ointment played a key role in ameliorating the progression of the disease. As a comparative, the patient had two neighbors with shingles, each of which experienced severe scabbing, itching, and pain associated with their shingles, despite taking an antiviral medication. The results of this study are consistent with the conclusion that MFG can play a role in stemming the progression of a disease caused by an enveloped virus.

The entire contents of all references cited in this disclosure are incorporated herein in their entireties, by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether such a range is separately disclosed. Where a range of numerical values is recited herein, unless otherwise stated, the range is intended to include the endpoints thereof, and all integers and fractions within the range. It is not intended that the scope of the invention be limited to the specific values recited when defining a range.

All patents, patent applications, and publications mentioned herein are incorporated herein in their entireties, by reference, unless indicated otherwise.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for treating a viral infection in an oropharyngeal cavity of a patient, the viral infection being caused by an enveloped virus selected from the group consisting of SARS-CoV-2 coronavirus, Epstein Barr Virus (EBV), and Herpesviruses, wherein the enveloped virus (1) can be transmitted to another person through the oropharyngeal cavity, (2) uses a glycoprotein or ACE-2 protein in a cell membrane of a cell to initiate a binding event with the cell membrane, and (3) after the binding event, deposits viral genetic material inside the cell where the viral genetic material begins a replication process, the method comprising:

preparing a gargle composition by separating milk fat globules from milk obtained from a mammalian source, and mixing the separated milk fat globules with a liquid carrier selected from the group consisting of water, milk, fruit juice, a sugar solution, a sports drink, tea, chilled coffee, a mouth wash, and an ethanol-based liquid, to form the gargle composition, the gargle composition consisting of from 16% by weight to 80% by weight milk fat globules and the liquid carrier, the milk fat globules comprising an organized mammalian membrane containing glycoproteins and ACE-2 protein;

containing the gargle composition in a spray bottle;

administering the gar composition by spraying the gargle composition from the spray bottle into the oropharyngeal cavity; and gargling with the gargle composition in the oropharyngeal cavity, the gargling comprising gargling at least twice over a ten-day period.

2. The method of claim 1, further comprising:

testing a patient for a viral infection caused by SARS-CoV-2 coronavirus;

determining from the testing that the patient is infected with SARS-CoV-2 coronavirus; and administering to the patient, the gargling with the gargle composition, within five days of the determining.

3. The method of claim 1, wherein the enveloped virus is SARS-CoV-2 coronavirus.

4. The method of claim 1, wherein the preparing comprises mixing liquid or powdered milk fat globules with the liquid carrier to form the gargle composition.

5. The method of claim 1, wherein the gargling further comprises gargling with the gargle composition for at least three seconds, and expelling the gargle composition after the gargling with the gargle composition.

6. A method for treating a topical infection on skin, caused by an enveloped virus that binds with cell membranes containing heparin sulfate, the enveloped virus being selected from the group consisting of Herpesviruses, the method comprising:

preparing an antiviral composition by separating milk fat globules from milk obtained from a mammalian source, and mixing the separated milk fat globules with a pharmaceutically acceptable topical carrier, the antiviral composition consisting of from 10% by weight to 95% by weight milk fat globules obtained from a mammalian source, based on the total weight of the antiviral composition, and from 5% by weight to 90% by weight the pharmaceutically acceptable topical carrier, based on the total weight of the antiviral composition, wherein the milk fat globules comprise an organized mammalian membrane containing glycoproteins, and the pharmaceutically acceptable topical carrier consists of petrolatum, paraben, mineral oil, hemp oil, full spectrum hemp oil, broad spectrum hemp oil, CBD, purified CBD, full spectrum hemp oil with CBDA/CBD at about a 1:1 ratio, beeswax, vitamin A, vitamin D, vitamin E, or a combination thereof; and applying, to the topical infection on the skin, the antiviral composition.

7. The method of claim 6, wherein the composition consists of from 25% by weight to 75% by weight milk fat globules, based on the total weight of the composition.

8. The method of claim 7, wherein the pharmaceutically acceptable topical carrier is petrolatum.

9. The method of claim 6, wherein the composition consists of from 40% by weight to 60% by weight milk fat globules from a mammalian source, based on the total weight of the composition, and from 60% by weight to 40% by weight the pharmaceutically acceptable topical carrier.

10. The method of claim 8, wherein the composition is in the form of a lip balm, the pharmaceutically acceptable carrier consists of petrolatum, the topical infection on the skin is an infection on lips, and the method comprises applying the lip balm to the topical infection on the lips.

11. The method of claim 6, wherein the composition is in the form of a spray and the method comprises spraying the composition on the topical infection on the skin.

12. The method of claim 9, wherein the composition is in the form of a salve and the method comprises applying the salve to the topical infection on the skin.

13. The method of claim 1, wherein the enveloped virus is SARS-CoV-2 coronavirus.

14. The method of claim 1, further comprising:

testing a human for SARS-CoV-2 coronavirus;

determining from the testing that the human is infected with SARS-CoV-2 coronavirus; and administering to the human, the gargling with the gargle composition, within three days of the determining.

15. The method of claim 1, wherein the enveloped virus is Epstein Barr Virus.

16. The method of claim 1, further comprising:

testing a human for Epstein Barr Virus;

determining from the testing that the human is infected with an Epstein Barr Virus infection; and administering to the human, the gargling with the gargle composition, within three days of the determining, wherein the gargling with the gargle composition comprises gargling with the gargle composition three times per day during an active stage of the Epstein Barr Virus infection.

17. The method of claim 16, wherein the gargling with the gargle composition comprises gargling with the gargle composition three times per day over several weeks.

18. The method of claim 1, wherein the enveloped virus is a Herpesvirus.

19. The method of claim 1, further comprising:

testing a human for a Herpesvirus;

determining from the testing that the human is infected with a Herpesvirus; and administering to the human, the gargling with the gargle composition, within three days of the determining.

20. The method of claim 6, wherein the Herpesvirus is selected from Herpes simplex virus type-1 (HSV-1), Herpes simplex virus type-2 (HSV-2), and Herpes Zoster virus (HZV).

* * * * *